(12) United States Patent
Zahn et al.

(10) Patent No.: US 7,982,055 B2
(45) Date of Patent: Jul. 19, 2011

(54) HETEROCYCLIC FUSED SELENOPHENE MONOMERS

(75) Inventors: Steffen Zahn, Pennsburg, PA (US); Carrie A. Costello, Troy, NY (US); Mark McLaws, Ballston Lake, NY (US)

(73) Assignee: Konarka Technologies, Inc., Lowell, MA (US)

( * ) Notice: Subject to any disclaimer, the term of this patent is extended or adjusted under 35 U.S.C. 154(b) by 667 days.

(21) Appl. No.: 11/777,362

(22) Filed: Jul. 13, 2007

(65) Prior Publication Data
US 2009/0018348 A1    Jan. 15, 2009

(51) Int. Cl.
*C07D 495/02* (2006.01)
(52) U.S. Cl. .......................................... 549/50
(58) Field of Classification Search ............... 549/50
See application file for complete search history.

(56) References Cited

U.S. PATENT DOCUMENTS

| | | |
|---|---|---|
| 4,732,901 A | 3/1988 | Buckle |
| 5,300,575 A | 4/1994 | Jonas et al. |
| 6,585,914 B2 | 7/2003 | Marks et al. |
| 6,645,401 B2 | 11/2003 | Giles et al. |
| 6,676,857 B2 | 1/2004 | Heeney et al. |
| 6,695,978 B2 | 2/2004 | Worrall et al. |
| 6,709,808 B2 | 3/2004 | Lelental et al. |
| 7,071,289 B2 | 7/2006 | Sotzing |
| 7,125,479 B2 | 10/2006 | Sotzing |
| 7,700,008 B2 | 4/2010 | Hsu et al. |
| 7,722,785 B2 | 5/2010 | Hsu et al. |
| 2004/0010115 A1 | 1/2004 | Sotzingt |
| 2006/0074250 A1 | 4/2006 | Zahn et al. |
| 2006/0076557 A1 | 4/2006 | Waller |
| 2007/0170401 A1 | 7/2007 | Hsu et al. |
| 2007/0278453 A1 | 12/2007 | Zahn et al. |
| 2007/0278458 A1 | 12/2007 | Martello et al. |
| 2008/0023676 A1 | 1/2008 | Hsu |
| 2009/0140219 A1 | 6/2009 | Zahn |
| 2009/0278093 A1 | 11/2009 | Heeney et al. |

FOREIGN PATENT DOCUMENTS

| | | |
|---|---|---|
| EP | 1 318 163 | 6/2003 |
| EP | 1 652 850 A1 | 5/2006 |
| EP | 1 728 810 A1 | 12/2006 |
| EP | 1 754 736 | 2/2007 |
| EP | 2 014 664 A2 | 1/2009 |
| EP | 2 014 665 A2 | 1/2009 |
| JP | 2005-035955 A | 2/2005 |
| KR | 2003/0047749 | 6/2003 |

OTHER PUBLICATIONS

Konar, A, et al; "Selenolo [3,4-b] Selenophene—The Third 'Classical' Selenophene;" Tetrahydron, vol. 36, (1980) ;; 3317-3323.
Yasuike, Shuji; et al; "Syntheses of Novel Group 15 and 16 Thieno[2,-3-b], Thieno[e,4-b]-, and Thieno[3,2-b]-Heteroles;" Heterocycles, vol. 48, No. 10, 1997; pp. 1891-1894.
Yasuike, S., et al; "Syntheses of Novel Group 15 and 16 Thieno[2,3-b]-, Thieno[3,4-b]-, and Thieno [3,2-b]-Heteroles"; vol. 45, No. 10; 1997; pp. 1891-1894; XP-001537354.
Litvinov, V.P., et al; "Selenopheno[2,3-c] Thiopene—A Third Isomeric Selenophenothiophene"; vol. 20, No. 7; 1971; p. 1498; XP-002580629.
Kulik, W., et al; "Dimetalation of Isopropenylacetylene. Application in the Synthesis of 3-Methylselenophen, 3-Methylene-2,3-Dihydroselenophen and the Tellurium Analogues"; vol. 24, No. 21; 1983; pp. 2203-2204; XP-002580630.
Shuji Yasuike, et al; "Syntheses of Novel Group 15 and 16 Thieno[2,3-b]-, Thieno[3,4-b]-, and Thieno[3.2-b] Heteroles"; Heterocycles; vol. 45, No. 10; 1997; pp. 1891-1894; XP1537354.
Litvinov, V.P., et al; "Selenopheno[2,3-c]Thiophene—A Third Isomeric Selenophenothiophene"; Russian Chemcial Bulletin; vol. 20, No. 7; 1971; p. 1498; XP002580629.
Kulik, W., et al; "Dimetalation of Isopropenylacetylene Application in the Synthesis of 3-Methylselenophen, 3-Methylene-2,3-Dihydroselenophen and the Tellurium Analogues"; Tetrahedron Letters; vol. 24, No. 21; 1983; pp. 2203-2204; XP002580630.
John, J.A., et al; "Synthesis of Polyphenylene Derivatives by Thermolysis of Enediynes and Dialkynylaromateic Monomers"; Tetrahedron, Elsevier Science Publishers; vol. 53, No. 45; Nov. 10, 1997; pp. 15515-15534; XP004106381.
Shuji Yasuike, et al; "Synthesis of Novel Dithieno[2,3-b,3', 2'-f]- and Dithieno[3,4-b;3', 4'-f]Heteroepins Containing Group 14, 15 and 16 Heavier Elements"; Heterocycles; vol. 45, No. 10; Oct. 1, 1997; pp. 1899-1902; XP001539729.
Gronowitz, S.; "New Syntheses of 3-Bromo-Thiophene and 3,4-Dibromo-Thiophene"; Acta Chem. Scand.; vol. 13, No. 5; 1959; pp. 1045-1046; XP002594517.
Ye, X.-S., et al; "Synthetic Applications of 3,4-Bis9Trimethylsilyl)Thiophene: Unsymmetrically 3,4-Disubstituted Thiophenese and 3,4-Didehydrothiophene"; J. Org. Chem., vol. 62; 1997; pp. 1940-1954; XP002594518.
Konar. A, et al; "Selenolo[3,4-b]Selenophene—The Third "Classical" Selenophtene"; Tetrahedron; vol. 36, No. 22; pp. 3317-3323; 1980.
Yavuz, M.S., et al; "Optically Transparent Conducting Polymers from Fused Heterocycles"; Material Research Society Proceeding; vol. 965, (2007).
Ketcham, R.; "Synthesis of Tetrathiafulvalene Doubly Fused to the 3,4-Position of Selenophene"; J. Org. Chem.; vol. 49, pp. 1117-1119; 1984.

(Continued)

*Primary Examiner* — Taofiq A Solola
(74) *Attorney, Agent, or Firm* — Fish & Richardson P.C.

(57) ABSTRACT

A heterocyclic fused selenophenes and a method of making a heterocyclic fused selenophenes of formula (1):

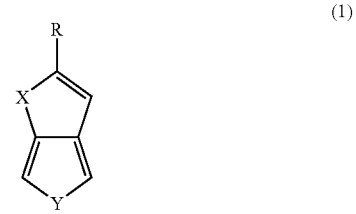

(1)

wherein X is S or Se, Y is S or Se, wherein one or both of X and Y is Se, R is a substituent group. The monomer being capable of polymerization to form an electrically conductive polymer or oligomer.

22 Claims, No Drawings

OTHER PUBLICATIONS

Abronin et al., "Quantum chemical analysis of selenium-77 chemical shifts in condensed selenophenes", Chem. Scripta (1982), 29(3), 75-7 (Abstract Only).

Beletskaya, et al., "The Heck Reaction As A Sharpening Stone of Palladium Catalysis," Chem. Rev. 2000, 100, pp. 3009-3066.

Fagnou, et al. "Rhodium-Catalyzed Carbon-Carbon Bond Forming Reactions of Organometallic Compounds", Chem. Rev. 2003, 103, pp. 169-196.

Guliev et al., "Quantum-chemical calculations of spectroscopic parameters of heteroaromatic sulfur and selenium compounds", Izvestiya Akademi Nauk SSSR, Seriya Khimicheskaya (1986), (10, 2251-3 (Abstract Only).

H Atom Adducts-New Free Radicals? J. Am. Chem. Soc. 85, 484 (1963).

Hassan et al., "Aryl-Aryl Bond Formation One Century After The Discovery of The Ullman Reaction", Chem. Rev. 2002, 102, pp. 1359-1469.

Jones, et al., "The Vilsmeir reaction of fully conjugated carbocycles and heterocycles", Organic Reactions (Hoboken, NJ) (1997), 49, no pages given (Abstract Only).

Miyaura et al., "Palladium-Catalyzed Cross-Coupling Reactions of Organoboron Compounds", Chem. Rev. 1995, 95, pp. 2457-2483.

Negishi, et al., Palladium-Catalyzed Alkynylation, Chem. Rev. 2003, 103, p. 1979-2017.

Novak "Structure, stability and aromaticity of bis-heteropentalenes", Theochem (1997, 398-399, 315-323 (Abstract Only).

Walker, et al., "New Chemically Conducting Pyrrole Blacks", J. Polym. Sci. Part A Polym. Chem., vol. 26, pp. 1285-1294 (1988).

HETEROCYCLIC FUSED SELENOPHENE MONOMERS

CROSS-REFERENCE TO RELATED APPLICATIONS

The subject matter of this application is related to U.S. patent application Ser. No. 11/777,386, filed on even date herewith, and entitled "SELENIUM CONTAINING ELECTRICALLY CONDUCTIVE POLYMERS AND METHOD OF MAKING ELECTRICALLY CONDUCTIVE POLYMERS"; the disclosure of which is hereby incorporated by reference.

BACKGROUND OF THE INVENTION

The present disclosure is directed to monomers and methods for making monomers for forming electrically conductive polymers.

Electrically conducting polymers have found use in a variety of organic optoelectronics applications. Such optoelectronic applications include polymeric light emitting diodes (thin film displays), solid-state lighting, organic photovoltaics, advanced memory devices, organic field effect transistors, ultracapacitors, electroluminescent devices, printed electronics, conductors, lasers, and sensors.

One of the first electrically conducting polymers was polyacetylene and the discovery of conductivity in such polymer created substantial interest in other types of electrically conducting polymers. Recently, conjugated poly(thiophenes) and substituted thiophene derivatives have been discovered to have electrically conducting properties. A feature of these polymers is that they can be cast into films and doped with conventional p- and n-type dopants. Additionally, the doped polymers can be cast into films and their electrical properties modified accordingly, thereby lending themselves suitable for use in a variety of optoelectronic applications.

Known thiophene monomers and electrically conducting polymers including thiophene and derivatives thereof include the following:

U.S. Patent Application Publication No. US2004/0010115A1 to Sotzing discloses homopolymers and copolymers comprised of repeating units of thieno[3,4-b]thiophene for use in electroactive applications. The thieno[3,4-b]thiophene compounds disclosed in the US2004/0010115A1 include the following structure:

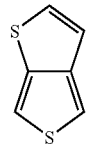

U.S. Patent Application Publication No. US2004/0010115A1 further discloses that copolymers can be formed with compounds including 3,4-ethylendioxythiophene, dithiophene, pyrrole, and benzothiophene.

U.S. Pat. No. 6,645,401 to Giles et al. discloses conjugated polymers of dithienothiophene (DTT) with vinylene or acetylene connecting groups as suitable for producing semiconductors or charge transport materials useful in electrooptical and electronic devices including field effect transistors ("FET"), photovoltaic, and sensor devices.

U.S. Pat. No. 6,585,914 to Marks discloses fluorocarbon-functionalized and/or heterocyclic modified poly (thiophenes) such as α, ω-diperfluorohexylsexithiophene for use in forming films, which behave as n-type semiconductors. These poly(thiophenes) also can be used to form thin film transistors with FET mobility.

U.S. Pat. No. 6,676,857 to Heeney et al. discloses polymers having polymerized units of 3-substituted-4-fluorothiophene as liquid crystal materials for use in semiconductors, charge transport materials, electrooptical field effect transistors, photovoltaic and sensor devices.

U.S. Pat. No. 6,695,978 to Worrall et al. discloses polymers of benzo[b]thiophene and bisbenzo[b]-thiophene and their use as semiconductors and as charge transport materials in electrooptical devices.

U.S. Pat. No. 6,709,808 to Lelental et al. discloses image-forming materials incorporating electrically conductive polymers based upon pyrrole-containing thiophene polymers and aniline containing polymers.

Tetrahedron 1940, 36, 3317-3324 by Gronowitz discloses the preparation of seleno(3,4-b)selenophene. The synthesis utilizes a decarboxylation procedure that is commonly seen as being problematic if exploited at a commercial scale.

Heterocycles 1997, 45, 1891-1894 discloses the preparation of selenolo(2,3-c)thiophene by a multistep route. Multistep routes have been shown to be useful for synthesizing materials at small scale, but are generally not favored for large scale, industrial setups.

While the above references include disclosures of known monomer compounds and methods of making these known monomer compounds, none of the above references discloses substituted seleno(3,4-b)selenophenes, seleno(2,3-c)thiophenes, or thiophene(3,4-b)selenophenes monomers or methods of making fused selenophene monomers of the present disclosure.

The disclosure of the foregoing patents, patent applications and publications is hereby incorporated by reference in their entirety.

What is needed is a monomer capable of forming an electrically conductive polymer for a wide range of electronic applications. There is also a need in this art for a monomer that can be formed using readily available, easily handled reagents and which can be polymerized.

BRIEF SUMMARY OF THE INVENTION

One aspect of the present disclosure includes a method of making a compound of formula (1):

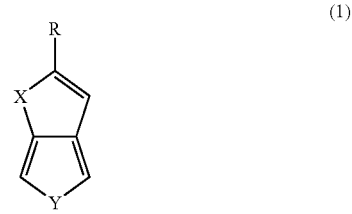

wherein X is S or Se, Y is S or Se, wherein one or both of X and Y is Se, R is a substituent group. R may be any substituent group capable of bonding to the ring structure. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms. The method includes providing a first reactant having the formula (2):

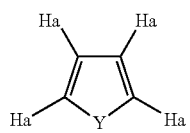

(2)

wherein Y is defined above and Ha is a halogen-containing group. The first reactant is reduced in the presence of a metal reducing agent to form a second reactant having the formula (3):

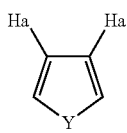

(3)

wherein Y and Ha are defined above. The second reactant is then reacted with a substituted 1-alkyne in the presence of a transition metal catalyst in order to form a third reactant, the third reactant having the formula (4):

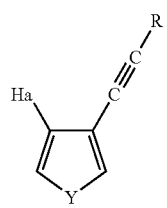

(4)

wherein R, Y and Ha are defined above. The third reactant is then reacted with an alkyl lithium in the presence of a compound comprising X, X being defined above, to produce a fourth reactant having the formula (5):

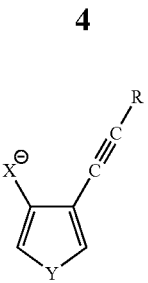

(5)

wherein R, X, and Y are defined above. The fourth reactant is then reacted with water to form the compound having formula (1).

Another aspect of the present disclosure includes a method for making heterocyclic fused selenophenes according to the following formula (4):

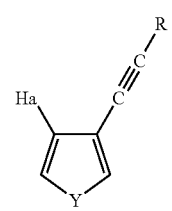

(4)

wherein X is S or Se, Y is S or Se, wherein one or both of X and Y is Se, R is a substituent group and may include the moieties discussed above with respect to formula (1). The method further includes providing a first reactant having the formula (2):

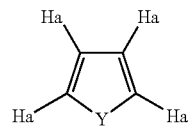

(2)

wherein X is defined above and Ha is a halogen-containing group. The first reactant is reduced in the presence of a metal reducing agent to form a second reactant having the formula (3):

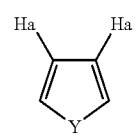

(3)

wherein Y and Ha are defined above. The second reactant is then reacted with a substituted 1-alkyne in the presence of a transition metal catalyst in order to form the compound according to formula (4):

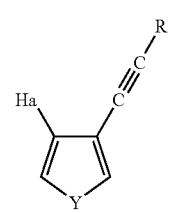

(4)

wherein Y, Ha and R are defined above.

Another aspect of the present disclosure includes a method of making a compound of formula (1):

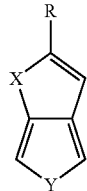

(1)

wherein X is S or Se, Y is S or Se, wherein one or both of X and Y is Se, R is a substituent group and may include the moieties discussed above with respect to formula (1). The method further includes providing a having the formula (4):

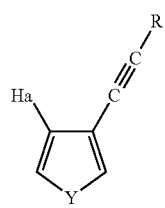

(4)

wherein R and Y are defined above and Ha is a halogen-containing group. The reactant is then reacted with an alkyl lithium in the presence of a compound comprising X, X being defined above, to produce a reactant having the formula (5):

(5)

wherein R, X, and Y are defined above. The fourth reactant is then reacted with water to form the compound having formula (1).

Another aspect of the present disclosure includes a method of making a compound of formula (6):

(6)

wherein X is S or Se, Y is S or Se, wherein one or both of X and Y is Se. The method further includes providing a reactant according to formula (7):

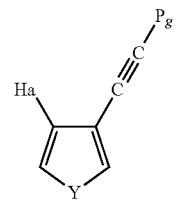

(7)

wherein Y is defined above and Ha is a halogen-containing group. $P_g$ is a hydrolysable protecting group. The reactant is then reacted with an alkyl lithium in the presence of a compound comprising X, X being defined above, to produce a reactant according to formula (8):

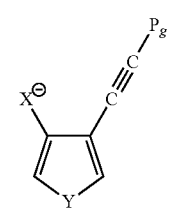

(8)

wherein $P_g$, X, and Y are defined above. The reactant is then reacted with water to form the compound having formula (6).

Another embodiment of the present disclosure includes heterocyclic monomer compounds according to the following formula:

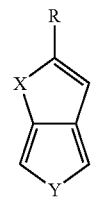

wherein X is S or Se, Y is S or Se, wherein one or both of X and Y is Se, R is a substituent group. R may include hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments, R may include alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms.

Another embodiment of the present disclosure includes heterocyclic fused compounds imidazolone, dioxolone, imidazolethione or dioxolethione including 2-phenyl-selenolo[2,3-c]thiophene (1a), 2-phenyl-selenolo[3,4-b]thiophene (1b) and 2-phenyl-selenolo[3,4-b]selenophene (1c), and the thiocarbonyl compounds 2-hexyl-selenolo[2,3-c]thiophene (1d), 2-hexyl-selenolo[3,4-b]thiophene (1e) and 2-hexyl-selenolo[3,4-b]selenophene (1f), all shown by the following structures:

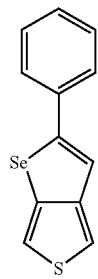

1a

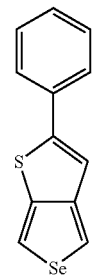

1b

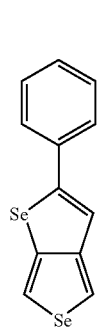

1c

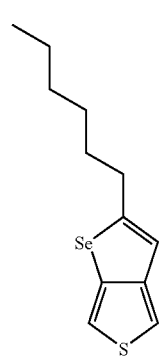

1d

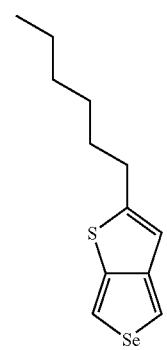

1e

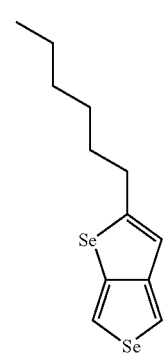

1f

Another embodiment of the present disclosure includes a heterocyclic monomer compound according to the following formula:

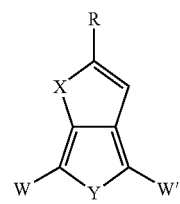

wherein X is S or Se, Y is S or Se, wherein one or both of X and Y is Se, R is a substituent group and may include the moieties discussed above with respect to formula (1)

Another embodiment of the present disclosure includes a compound having the following formula:

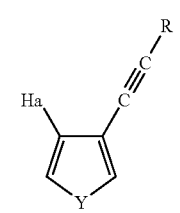

wherein Y is S or Se, R is a substituent group and may include the moieties discussed above with respect to formula (1) and Ha is a halogen-containing group.

Another embodiment of the present disclosure includes a compound having the following formula:

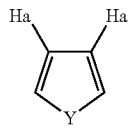

wherein Y is Se, Ha is a halogen containing group.

The disclosure includes heterocyclic fused selenophene based monomers. Such monomers and polymers derived therefrom, find use in applications, including, but not limited to, hole injection materials, charge transport materials, semiconductors, and/or conductors, in optical, electrooptical or electronic devices, polymeric light emitting diodes (i.e., PLED), electroluminescent devices, organic field effect transistors (i.e., FET or OFET), flat panel display applications (e.g., LCD's), radio frequency identification (i.e., RFID) tags, printed electronics, ultracapacitors, organic photovoltaics (i.e., OPV), sensors, lasers, small molecule or polymer based memory devices, electrolytic capacitors, anti-corrosion coatings, or as hydrogen storage materials.

One advantage of a method according to an embodiment of the present disclosure includes preparation of previously unknown substituted selenophene monomers having an extended range of performance in many electronic applications.

Another advantage of a method according to an embodiment of the present disclosure includes preparation of heterocyclic fused selenophene monomers. In one aspect the inventive methods can be conducted without the necessity of using decarboxylation chemistries.

Still another advantage of a method according to an embodiment of the present disclosure includes preparation of heterocyclic selenophene monomers in high yield, providing for an efficient, cost effective process. For example, the inventive process can produce a monomeric product having at least about 65 mol % monomer.

An advantage of an embodiment of the present disclosure is that heterocyclic fused selenophene monomers and derivatives thereof may be used to produce conductive polymers having low work functions (e.g., polymers a conductivity of at least about $10^{-5}$ S/cm). For example, the present disclosure includes monomers for fabricating polymers suitable as a hole injecting material.

Another advantage of an embodiment of the present disclosure is that heterocyclic fused selenophene monomers and derivatives thereof may be used to produce conducting polymers having a low band gap (e.g., a band gap of about <2.5 eV). For example, the present disclosure includes monomers for fabricating polymers suitable as transparent conductors.

Still another advantage of an embodiment of the present disclosure is that heterocyclic fused selenophene monomers and derivatives thereof may be used to produce conducting polymers having a wide range of electronic applications.

Still another advantage of an embodiment of the present disclosure is that heterocyclic fused selenophene monomers and derivatives thereof may be used to produce a hole injection material having desirable properties including a substantially identical work function level between the hole injection layer ("HIL") material and the light emitting layer in an electroluminescent device.

Still another advantage of an embodiment of the present disclosure is that heterocyclic fused selenophene monomers and derivatives thereof may be used to produce an oxidized form of the polymer. The resultant polymer can possess desirable properties including the formation of a highly delocalized ionic polymer having high conductivity.

Still another advantage of an embodiment of the present disclosure is that heterocyclic fused selenophene monomers and derivatives thereof may be used to produce solution processible materials.

Still another advantage of an embodiment of the present disclosure is that monomers based upon heterocyclic fused selenophenes and derivatives thereof may be used to produce an environmentally stable semiconducting polymer.

Other features and advantages of the present disclosure will be apparent from the following more detailed description of certain embodiments, taken in conjunction with the accompanying drawings which illustrate, by way of example, the principles of the disclosure.

DETAILED DESCRIPTION OF THE INVENTION

"Fused" is defined as sharing a common bond within the ring between a thiophene and a selenophene or a selenophene and a selenophene, thereby connecting the ring structures together.

The disclosure includes a method for making heterocyclic fused selenophenes according to the following formula (1):

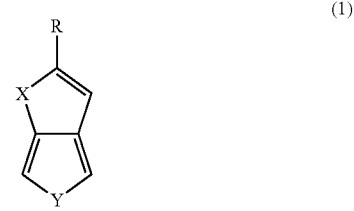

(1)

wherein X is S or Se, Y is S or Se, wherein one or both of X and Y is Se, R is a substituent group. R may be any substituent group capable of bonding to the ring structure. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms. The method further includes providing a first reactant having the formula (2):

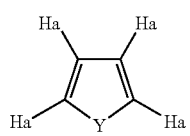

(2)

wherein Y is defined above and Ha is a halogen containing group. The halogen containing group may include, but is not limited to, Cl, Br or I. The first reactant is reduced in the presence of a metal reducing agent to form a second reactant having the formula (3):

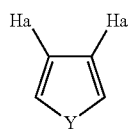

(3)

wherein Y and Ha are defined above. The metal reducing agent may include any metal reducing agent suitable for reducing the first reactant and may include, but is not limited to zinc or magnesium. The second reactant is then reacted with a substituted 1-alkyne in the presence of a transition metal catalyst in order to form a third reactant, the third reactant having the formula (4):

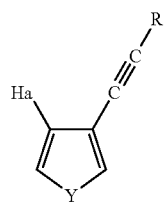

(4)

wherein R, Y and Ha are defined above. The transition metal catalyst may include, but is not limited to, platinum group containing catalysts, such as palladium dichloride-bis-triphenylphosphine or other systems that may be used in Sonogashira coupling chemistry. The substituted 1-alkyne includes functional groups having the following formula:

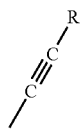

R may be any substituent group capable of bonding to the triple bonded carbon. R may include alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms. The third reactant is then reacted with an alkyl lithium in the presence of a compound comprising X, X being defined above, to produce a fourth reactant having the formula (5):

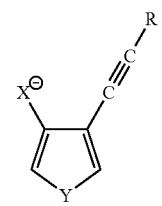

(5)

wherein R, X, and Y are defined above. The alkyl lithium may include alkyl containing lithium compounds, such as, but not limited to n-butyl, secondary and tertiary-butyl lithium or other alkyl lithium agents. The compound comprising X may include compounds that contain sulfur, selenium or combinations thereof. Suitable compounds include, but are not limited to selenium powder and sulfur ($S_8$). The fourth reactant is then reacted with water to form the compound having formula (1).

This disclosure provides a method for making heterocyclic fused selenophenes according to the following formula (4):

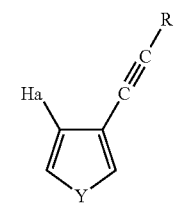

(4)

wherein X is S or Se, Y is S or Se, wherein one or both of X and Y is Se, R is a substituent group and may include the moieties discussed above with respect to formula (1). The third reactant is then reacted with an alkyl lithium in the presence of a compound comprising X, X being defined above, to produce a fourth reactant having the formula (5):

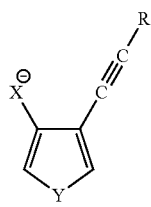

(5)

wherein R, X, and Y are defined above. The fourth reactant is then reacted with water to form the compound having formula (1).

The present disclosure further includes a method of making a compound of formula (1):

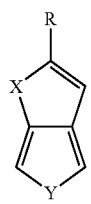

(1)

wherein X is S or Se, Y is S or Se, wherein one or both of X and Y is Se, R is a substituent group and may include the moieties discussed above with respect to formula (1). The method further includes providing a having the formula (4):

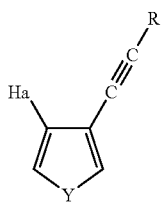

(4)

wherein R, Y and Ha are defined above. The reactant is then reacted with an alkyl lithium in the presence of a compound comprising X, X being defined above, to produce a reactant having the formula (5):

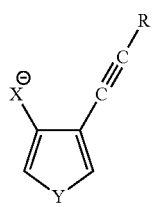

(5)

wherein R, X, and Y are defined above. The fourth reactant is then reacted with water to form the compound having formula (1).

The present disclosure further includes a method of making a compound of formula (1):

(6)

wherein X is S or Se, Y is S or Se, wherein one or both of X and Y is Se. The method further includes providing a compound having the formula (7):

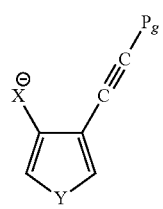

(7)

wherein Y and Ha are defined above. $P_g$ is a hydrolysable protecting group. The hydrolysable protecting group may be any suitable protecting group that is capable of hydrolyzing and may include, but is not limited to trimethyl silyl or tert-butyldimethyl silyl. The reactant is then reacted with an alkyl lithium in the presence of a compound comprising X, X being defined above, to produce a reactant having the formula (8):

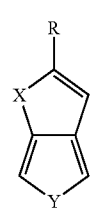

(8)

wherein $P_g$, X, Y and Ha are defined above. The reactant is then reacted with water to form the compound having formula (6).

This disclosure further includes heterocyclic fused selenophene monomeric compounds according to the following formula (1):

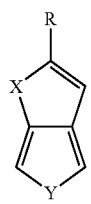

(1)

wherein X is S or Se, Y is S or Se, wherein one or both of X and Y is Se, R is a substituent group. R may be any substituent group capable of bonding to the ring structure. R may include hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms Another embodiment of the present disclosure includes heterocyclic fused selenophene compounds including 2-phenyl-selenolo[2,3-c]thiophene (1a), 2-phenyl-selenolo[3,4-b]thiophene (1b) and 2-phenyl-selenolo[3,4-b]selenophene (1c), and the thiocarbonyl compounds 2-hexyl-selenolo[2,3-c]thiophene (1d), 2-hexyl-selenolo[3,4-b]thiophene (1e) and 2-hexyl-selenolo[3,4-b]selenophene (1f), all shown by the following structures:

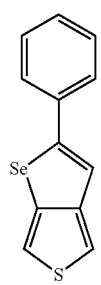
1a

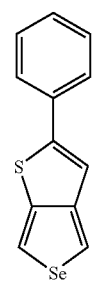
1b

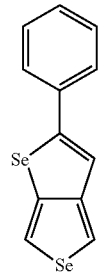
1c

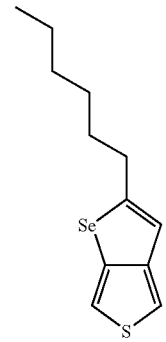
1d

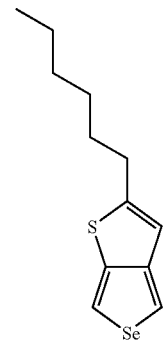
1e

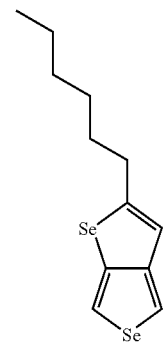
1f

In another embodiment of the present disclosure, derivatives of the heterocyclic fused selenophenes formed prior to or after the formation of the fully aromatic fused heterocyclic monomer.

Another embodiment of the present disclosure includes a compound having the following formula:

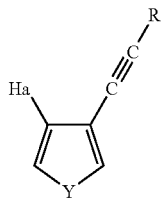

wherein Y is S or Se, R is a substituent group and may include the moieties discussed above with respect to formula (1) and Ha is a halogen containing group.

Another embodiment of the present disclosure includes a compound having the following formula:

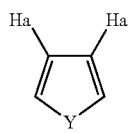

wherein Y is Se, Ha is a halogen containing group. In certain embodiments Ha is independently Br or I and combinations of Br and I on the same molecule.

Monomer derivatives according to the present disclosure may include compounds having the following formula:

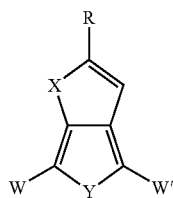

wherein X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C-atoms. W and W' are H, halogen atoms, e.g., F, Cl, Br, and I, metallorganics, e.g., MgCl, MgBr, MgI, $Sn(R_2)_3$, where $R_2$ is $C_{1-6}$ alkyl or $C_{1-6}$ alkyl ether, boronic acid, boronic ester, vinyl units, e.g., —CH=$CHR_3$ where $R_3$ is H or $C_{1-6}$ alkyl, ether, i.e., —$OC_{1-6}$ alkyl, esters, i.e., —$COOC_{1-6}$ alkyl, —S—$COR_4$ and —$COR_4$ where $R_4$ is H or $C_{1-6}$ alkyl, —C≡CH, and polymerizable aromatic rings such as phenyl, naphthalene, pyrrole, and thiophene. Derivatives of the substituted claimed compositions can be formed prior to or after addition of the secondary or tertiary functionality.

The polymerization and the resulting polymer can be controlled by selecting moieties W and W' having the desired polymerization reaction and desired resultant polymer. Carbon-carbon bond forming reactions may be completed following any suitable method. Methods suitable for use with the monomer of the present disclosure include, but are not limited to the Suzuki Reactions, the Yamamoto Reactions, the Heck Reactions, the Stille Reactions, the Sonogashira-Hagihara Reactions, the Kumada-Corriu Reactions, the Riecke Reactions, and the McCullogh Reactions.

Derivatives according to the present disclosure may include homopolymers and copolymers in which W and W' are H. In another embodiment, the compounds of the present disclosure may include homopolymer and copolymers wherein W, and W' are Br. In still another embodiment, the compounds of the present disclosure may include homopolymer and copolymers wherein W, and W' are trialkylstannyl.

Many of the derivatives of the respective monomers where W and W' are other than H are formed post-formation of the monomers. In one such post-reaction, one or both hydrogen atoms may be replaced with other functional groups such as bromide or trialkylstannyl groups. The replacement of the hydrogen atoms may take place using any reaction mechanism suitable for use with heterocyclic ring structures. In an alternate embodiment, the W and/or W' containing derivatives may be formed prior to converting thiophene to the first reaction product (e.g., 3,4-dihydroxythiophene) and then undergoing a reaction procedure shown above for the conversion of 3,4-dihydroxythiophene or 3,4-dihydroxyselenophene derivatives to the imidazolone, dioxolone, imidazolethione or dioxolethione based monomers where the W and W' are compatible with the chemistry outlined above.

EXAMPLES

The following examples are provided to illustrate various embodiments and comparisons and are not intended to restrict the scope of the disclosure. The structure of the compounds formed by the following Examples was confirmed by using NMR in accordance with conventional methods.

Example 1

The compound selenolo[2,3-c]thiophene was prepared in a single reaction mixture in accordance with the method of the present disclosure.

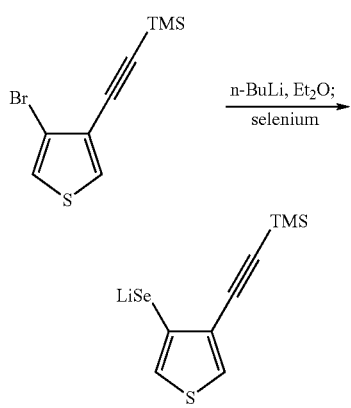

A solution of 2-bromomethyl-4-trimethylsilanyl-but-1-en-3-yne-1-thiol (5.00 g, 19.3 mmol) in ether (19.3 mL) under N₂ was cooled to −80° C. Maintaining the temperature below −50° C., n-butyl lithium (2.5 M in hexanes, 7.60 mL, 19.3 mmol) was added. The reaction was allowed to warm to −20° C. and then was cooled to −30° C. Selenium powder (1.60 g, 20.3 mmol) was added in one portion and stirred at −5° C. for 1 h. The reaction was cooled to −30° C., water (19.3 mL) was added, and the mixture was agitated vigorously for 20 seconds. The phases were split immediately. The ether layer was extracted with cold water (5.00 mL). The aqueous layers were combined and heated to 70° C. for 1.5 h. Upon cooling to room temperature the reaction mixture was extracted with MTBE (3×20.0 mL). The combined MTBE extracts were dried over magnesium sulfate and concentrated to an oil. The crude oil was purified by column chromatography (silica gel, cyclohexane) to provide selenolo[2,3-c]thiophene as an oil (2.30 g, 12.3 mmol, 63.7 mol %): 500 MHz ¹H NMR (DMSO-d₆) δ 7.96 (d, J=6.0 Hz, 1H), 7.69 (d, J=2.6 Hz, 1H), 7.61 (dd, J=2.7, 0.6 Hz, 1H), 7.25 (d, J=6.0 Hz, 1H); 125 MHz ¹³C NMR (DMSO-d₆) δ 149.6, 135.4, 133.5, 120.2, 115.1, 114.8; 76 MHz ⁷⁷Se NMR (DMSO-d₆) δ 429.3 (dd, J {⁷⁷Se-¹H}=47.0, 7.6 Hz); UV-Vis λ$_{max}$=243.9 nm (CH₂Cl₂); IR (ATR) ν 3096, 1548, 1483, 1422, 1340, 1278, 1169, 1070, 982, 834, 758, 726 cm⁻¹; MS (+APCI) m/z (M+1)=189.

Example 2

The compound selenolo[3,4-b]selenophene was prepared in a series of reactions in accordance with the method of the present disclosure.

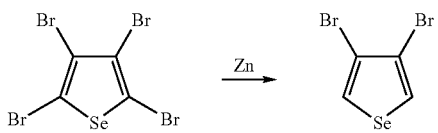

To a stirred slurry of 2,3,4,5-tetrabromo-selenophene (6.20 g, 13.9 mmol) in acetic acid (10.0 mL) and water (20.0 mL) under N₂ was added zinc (2.90 g, 45.1 mmol). The mixture was heated to 100° C. for 3 h. The reaction mixture was extracted with MTBE. The MTBE extracts were quenched with saturated sodium bicarbonate until the pH was 7-8. The organic was dried over sodium sulfate, filtered, and concentrated to an oil. The crude oil was purified by column chromatography (silica gel, heptane) to provide 3,4-dibromo-selenophene (1.95 g, 6.75 mmol, 48.6 mol %): 500 MHz ¹H NMR (CDCl₃) δ 7.93 (s, 2H); 125 MHz ¹³C NMR (CDCl₃) δ 127, 114.

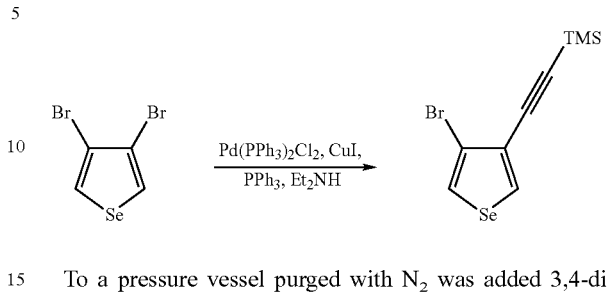

To a pressure vessel purged with N₂ was added 3,4-dibromo-selenophene (3.69 g, 12.77 mmol), DMF (10.0 mL), triphenylphosphine (0.669 g, 2.55 mmol), copper(I) iodide (0.161 g, 0.843 mmol), diethylamine (dried over KOH, 20.0 mL, 191.55 mmol), (trimethylsilyl)acetylene (0.910 mL, 6.39 mmol), and palladium dichloride-bis-triphenylphosphine (0.592 g, 0.843 mmol). The reaction vessel was sealed and the mixture heated to 90° C. for 1 h. Upon cooling to room temperature, the reaction mixture was diluted with MTBE (100.0 mL) and was washed with 0.1 M HCl (3×50.0 mL). The combined aqueous layers were extracted with MTBE (50.0 mL). The combined MTBE extracts were quenched with saturated sodium bicarbonate (50.0 mL), dried over magnesium sulfate, and concentrated to an oil. The crude oil was purified by column chromatography (silica gel, cyclohexane) to provide (4-Bromo-selenophen-3-ylethynyl)-trimethyl-silane (1.55 g, 5.08 mmol, 79.5 mol %): 500 MHz ¹H NMR (CDCl₃) δ 8.15 (d, J=2.9 Hz, 1H), 7.58 (d, J=2.9 Hz, 1H), 0.26 (S, 9h); 125 MHz ¹³C NMR (CDCl₃) δ 135.4, 127.0, 126.4, 114.1, 99.8, 96.8, 0.2.

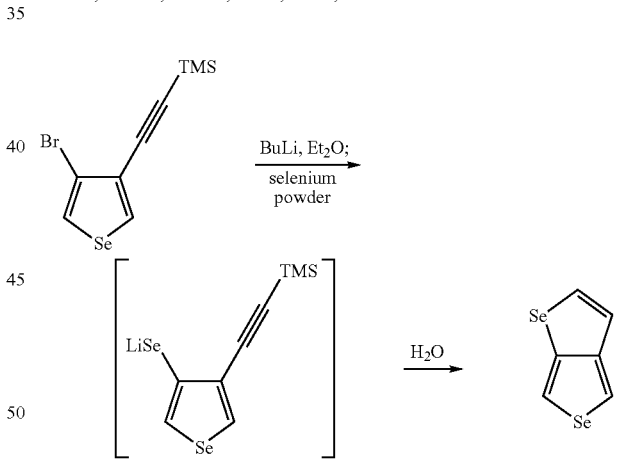

A solution of (4-bromo-selenophen-3-ylethynyl)-trimethyl-silane (1.51 g, 4.95 mmol) in ether (6.00 mL) under N₂ was cooled to −65° C. Maintaining the temperature above—50° C., n-butyl lithium (2.5 M in hexanes, 1.98 mL, 4.99 mmol) was added. The reaction was allowed to warm to −20° C., and then was cooled back to −30° C. Selenium powder (0.410 g, 5.20 mmol) was added in one portion and stirred at −5° C. for 1 h. The reaction was cooled to −30° C., water (6.00 mL) was added, and the mixture was agitated vigorously for 20 seconds. The phases were split immediately. The ether layer was extracted with cold water (6.00 mL). The aqueous layers were combined and heated to 70° C. for 1 h. Upon cooling to room temperature the reaction was extracted with MTBE (2×20.0 mL). The combined MTBE extracts were dried over magnesium sulfate and concentrated to an oil. The crude oil was purified by column chromatography (silica gel, cyclohexane; and 4:1 cyclohexane/pentane). The crude material was recrystallized from pentane to provide Selenolo[3,4-b]selenophene as an off-white solid (0.127 g, 0.543 mmol, 11.0 mol %): 500 MHz $^1$H NMR (DMSO-$d_6$) δ 8.29 (d, J=2.3 Hz, 1H), 8.17 (dd, J=2.2, 0.6 Hz, 1H), 8.02 (d, J=6.0 Hz, 1H), 7.11 (d, J=6.0 Hz, 1H); 125 MHz $^{13}$C NMR (DMSO-$d_6$) δ 152.0, 136.4, 132.7, 121.3, 120.8, 119.5; 76 MHz $^{77}$Se NMR (DMSO-$d_6$) δ 734.5 (t, J{$^{77}$Se-$^1$H}=46.5 Hz), 429.3 (dd, J{$^{77}$Se-$^1$H}=46.4, 7.1 Hz); UV-Vis $\lambda_{max}$=249.5 nm (MeOH); IR (ATR) ν 3100, 1548, 1493, 1437, 1318, 1272, 1152, 1108, 1067, 967, 895, 756, 730 cm$^{-1}$; MS (+APCI) m/z (M+1)=237.

Example 3

The compound selenolo[3,4-b]thiophene was prepared in a series of reactions in accordance with the method of the present disclosure.

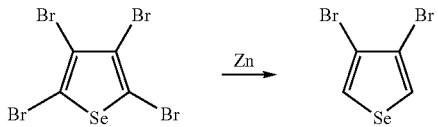

To a stirred slurry of 2,3,4,5-tetrabromo-selenophene (6.20 g, 13.9 mmol) in acetic acid (10.0 mL) and water (20.0 mL) under $N_2$ was added zinc (2.90 g, 45.1 mmol). The mixture was heated to 100° C. for 3 h. The reaction mixture was extracted with MTBE. The MTBE extracts were quenched with saturated sodium bicarbonate until the pH was 7-8. The organic was dried over sodium sulfate, filtered, and concentrated to an oil. The crude oil was purified by column chromatography (silica gel, heptane) to provide 3,4-dibromo-selenophene (1.95 g, 6.75 mmol, 48.6 mol %): 500 MHz $^1$H NMR (CDCl$_3$) δ 7.93 (s, 2H); 125 MHz $^{13}$C NMR (CDCl$_3$) δ 127, 114.

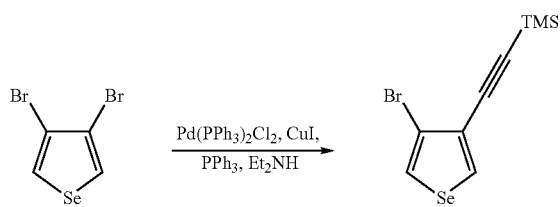

To a pressure vessel purged with $N_2$ was added 3,4-dibromo-selenophene (3.69 g, 12.77 mmol), DMF (10.0 mL), triphenylphosphine (0.669 g, 2.55 mmol), copper(I) iodide (0.161 g, 0.843 mmol), diethylamine (dried over KOH, 20.0 mL, 191.55 mmol), (trimethylsilyl)acetylene (0.910 mL, 6.39 mmol), and palladium dichloride-bis-triphenylphosphine (0.592 g, 0.843 mmol). The reaction vessel was sealed and the mixture heated to 90° C. for 1 h. Upon cooling to room temperature, the reaction mixture was diluted with MTBE (100.0 mL) and was washed with 0.1 M HCl (3×50.0 mL). The combined aqueous layers were extracted with MTBE (50.0 mL). The combined MTBE extracts were quenched with saturated sodium bicarbonate (50.0 mL), dried over magnesium sulfate, and concentrated to an oil. The crude oil was purified by column chromatography (silica gel, cyclohexane) to provide (4-bromo-selenophen-3-ylethynyl)-trimethyl-silane (1.55 g, 5.08 mmol, 79.5 mol %): 500 MHz $^1$H NMR (CDCl$_3$) δ 8.15 (d, J=2.9 Hz, 1H), 7.58 (d, J=2.9 Hz, 1H), 0.26 (S, 9h); 125 MHz $^{13}$C NMR (CDCl$_3$) δ 135.4, 127.0, 126.4, 114.1, 99.8, 96.8, 0.2.

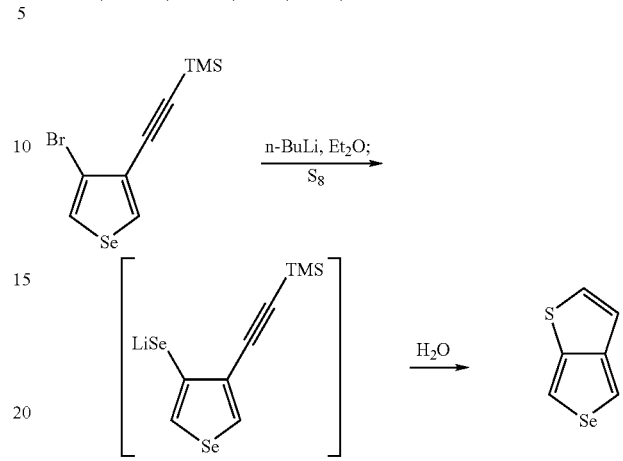

A solution of (4-bromo-selenophen-3-ylethynyl)-trimethyl-silane (R=TMS, 1.90 g, 6.23 mmol) in ether (7.40 mL) under $N_2$ was cooled to −70° C. Maintaining the temperature below −50° C., n-butyl lithium (2.5 M in hexanes, 2.50 mL, 6.23 mmol) was added. The reaction was allowed to warm to −20° C. and then cooled back to −30° C. Sulfur (0.210 g, 6.54 mmol) was added in one portion and stirred at 0° C. for 1 h. The reaction was cooled to −30° C.; water (7.40 mL) was added and agitated vigorously for 20 seconds. The phases were split immediately. The ether layer was extracted with cold water (4.00 mL). The aqueous layers were combined and heated to 70° C. for 1.5 h. Upon cooling to room temperature the reaction was extracted with MTBE (3×20.0 mL). The combined MTBE extracts were dried over magnesium sulfate and concentrated to an oil. The crude oil was purified by column chromatography (silica gel, cyclohexane) to provide selenolo[3,4-b]thiophene as an oil (0.344 g, 1.84 mmol, 29.5 mol %): 500 MHz $^1$H NMR (DMSO-$d_6$) δ 8.24 (d, J=2.3 Hz, 1H), 8.18 (dd, J=2.3, 0.8 Hz, 1H), 7.68 (d, J=5.7 Hz, 1H), 6.88 (d, J=5.7 Hz, 1H); 125 MHz $^{13}$C NMR (DMSO-$d_6$) δ 149.7, 140.0, 133.0, 119.0, 117.4, 116.4; 76 MHz $^{77}$Se NMR (DMSO-$d_6$) δ 739.7 (t, J{$^{77}$Se-$^1$H}=46.6 Hz); UV-Vis $\lambda_{max}$=248.3 nm (CH$_2$Cl$_2$); IR (ATR) ν 3095, 1549, 1488, 1319, 1289, 1152, 1077, 989, 804, 748 cm$^{-1}$; MS (+APCI) m/z (M+1)=189.

Example 4

The monomers can be readily derivatised in the 2-position according to the disclosure providing new compositions of matter. This example illustrates the preparation of 2-phenyl-selenolo[3,4-b]selenophene, which was prepared in a series of reactions in accordance with the method of the present disclosure.

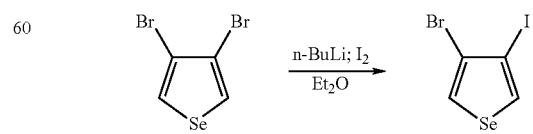

A solution of 3,4-dibromo-selenophene (2.36 g, 8.17 mmol) in ether (24.0 mL) under $N_2$ was cooled to −70° C.

Maintaining the temperature below −50° C. n-butyl lithium (2.5 M in hexanes, 3.43 mL, 8.58 mmol) was added. Iodine chips (2.28 g, 8.99 mmol) were added and the reaction mixture was warmed to 0° C. over at least 1 h. After addition of MTBE (50.0 mL), the reaction was quenched with saturated sodium bicarbonate (20.0 mL). The phases were split and the MTBE/ether extract was quenched with additional saturated sodium bicarbonate (20.0 mL). The combined MTBE/ether extracts were dried over magnesium sulfate and concentrated to an oil. The oil was purified by column chromatography (silica gel, cyclohexane). The combined fractions in cyclohexane were treated with sodium metabisulfite, filtered, and concentrated to provide 3-bromo-4-iodo-selenophene as an oil (1.97 g, 5.87 mmol, 71.8 mol %): 300 MHz $^1$H NMR (CDCl$_3$) δ 8.1 (d, J=3.0 Hz, 1H), 7.89 (d, J=3.0 Hz, 1H).

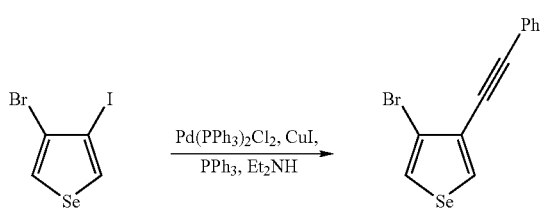

To a pressure vessel purged with N$_2$ was added 3-bromo-4-iodo-selenophene (1.97 g, 5.87 mmol), DMF (5.20 mL), triphenylphosphine (0.307 g, 1.17 mmol), copper(I) iodide (0.0740 g, 0.387 mmol), diethylamine (dried over KOH, 9.20 mL, 88.0 mmol), phenyl acetylene (0.645 mL, 5.87 mmol), and palladium dichloride-bis-triphenylphosphine (0.272 g, 0.387 mmol). The reaction vessel was sealed and the mixture heated to 70° C. for 1 h. Upon cooling to room temperature, the reaction mixture was diluted with MTBE (50.0 mL) and was washed with 0.1 M HCl (3×30.0 mL). The combined aqueous layers were extracted with MTBE (30.0 mL). The MTBE rich layer was dried over magnesium sulfate and concentrated to an oil. The crude oil was purified by column chromatography (silica gel, cyclohexane) to provide 3-bromo-4-phenylethynyl-selenophene (1.07 g, 3.19 mmol, 54.3 mol %): 500 MHz $^1$H NMR (CDCl$_3$) δ 8.18 (d, J=2.9 Hz, 1H), 7.90 (d, J=2.9 Hz, 1H), 7.58-7.54 (m, 2H), 7.36-7.32 (m, 3H); 125 MHz $^{13}$C NMR (CDCl$_3$) δ 134.2, 131.7, 128.5, 128.4, 126.8, 126.3, 122.9, 114.1, 91.0, 84.7.

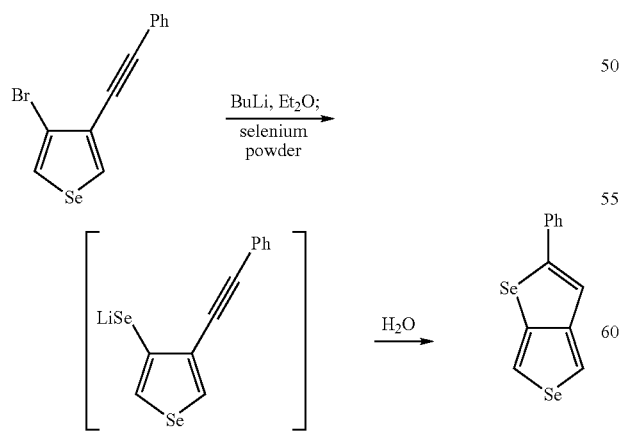

A solution of 3-bromo-4-phenylethynyl-selenophene (2.00 g, 6.45 mmol) in ether (26.0 mL) under N$_2$ was cooled to −65° C. Maintaining the temperature below −50° C. tert-butyl lithium (1.7 M in pentane, 7.59 mL, 12.9 mmol) was added. The reaction was stirred at −60 to −50° C. for 0.5 h. Selenium powder (0.530 g, 6.71 mmol) was added in one portion; the mixture was allowed to warm to room temperature over 2 h and was held for 1 h. The solvent was evaporated and a solution of potassium hydroxide (0.434 g, 7.74 mmol) in methanol (25.0 mL) was added and heated to reflux for 15 h. Upon cooling to room temperature the reaction was concentrated to an oil, dissolved in CH$_2$Cl$_2$ and extracted with water. The aqueous layer was extracted with CH$_2$Cl$_2$. The combined organic layers were dried over magnesium sulfate and concentrated to a crude residue. The crude material was recrystallized from CH$_2$Cl$_2$ and methanol to provide 2-phenyl-selenolo[3,4-b]selenophene as a light orange powder (0.571 g, 1.84 mmol, 40.8 mol %): 500 MHz $^1$H NMR (DMSO-d$_6$) δ 8.34 (d, J=2.3 Hz, 1H), 8.22 (dd, J=2.2, 0.6 Hz, 1H), 7.62-7.59 (m, 2H), 7.57 (s, 1H), 7.45-7.42 (m, 2H), 7.39-7.35 (m, 1H); 125 MHz $^{13}$C NMR (DMSO-d$_6$) δ 151.9, 148.3, 136.0, 134.6, 129.1, 128.5, 125.9, 122.6, 119.9, 116.9; 95 MHz $^{77}$Se NMR (DMSO-d$_6$) δ 731.2 (t, J{$^{77}$Se-$^1$H}=45.8 Hz), 427.7 (d, J{$^{77}$Se-$^1$H}=3.8 Hz); UV-Vis λ$_{max}$=309.3 nm (CH$_2$Cl$_2$); IR (ATR) v 3088, 1553, 1482, 1438, 1327, 1303, 1221, 1152, 1074, 1028, 901, 843, 827, 750, 683 cm$^{-1}$; MS (+APCI) m/z(M+1)=313.

Example 5

The monomers can be readily derivatised in the 2-position according to the disclosure providing new compositions of matter. This example illustrates the preparation of 2-phenyl-selenolo[3,4-b]thiophene, which was prepared in a series of reactions in accordance with the method of the present disclosure.

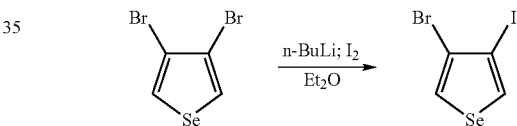

A solution of 3,4-dibromo-selenophene (2.36 g, 8.17 mmol) in ether (24.0 mL) under N$_2$ was cooled to −70° C. Maintaining the temperature below −50° C. n-butyl lithium (2.5 M in hexanes, 3.43 mL, 8.58 mmol) was added. Iodine chips (2.28 g, 8.99 mmol) were added and the reaction mixture was warmed to 0° C. over at least 1 h. After addition of MTBE (50.0 mL), the reaction was quenched with saturated sodium bicarbonate (20.0 mL). The phases were split and the MTBE/ether extract was quenched with additional saturated sodium bicarbonate (20.0 mL). The combined MTBE/ether extracts were dried over magnesium sulfate and concentrated to an oil. The oil was purified by column chromatography (silica gel, cyclohexane). The combined fractions in cyclohexane were treated with sodium metabisulfite, filtered, and concentrated to provide 3-bromo-4-iodo-selenophene as an oil (1.97 g, 5.87 mmol, 71.8 mol %): 300 MHz $^1$H NMR (CDCl$_3$) δ 8.1 (d, J=3.0 Hz, 1H), 7.89 (d, J=3.0 Hz, 1H).

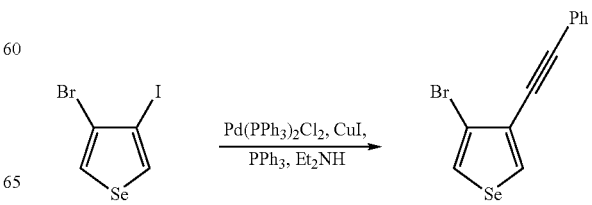

To a pressure vessel purged with $N_2$ was added 3-bromo-4-iodo-selenophene (1.97 g, 5.87 mmol), DMF (5.20 mL), triphenylphosphine (0.307 g, 1.17 mmol), copper(I) iodide (0.0740 g, 0.387 mmol), diethylamine (dried over KOH, 9.20 mL, 88.0 mmol), phenyl acetylene (0.645 mL, 5.87 mmol), and palladium dichloride-bis-triphenylphosphine (0.272 g, 0.387 mmol). The reaction vessel was sealed and the mixture heated to 70° C. for 1 h. Upon cooling to room temperature, the reaction mixture was diluted with MTBE (50.0 mL) and was washed with 0.1 M HCl (3×30.0 mL). The combined aqueous layers were extracted with MTBE (30.0 mL). The MTBE rich layer was dried over magnesium sulfate and concentrated to an oil. The crude oil was purified by column chromatography (silica gel, cyclohexane) to provide 3-bromo-4-phenylethynyl-selenophene (1.07 g, 3.19 mmol, 54.3 mol %): 500 MHz $^1$H NMR (CDCl$_3$) δ 8.18 (d, J=2.9 Hz, 1H), 7.90 (d, J=2.9 Hz, 1H), 7.58-7.54 (m, 2H), 7.36-7.32 (m, 3H); 125 MHz $^{13}$C NMR (CDCl$_3$) δ134.2, 131.7, 128.5, 128.4, 126.8, 126.3, 122.9, 114.1, 91.0, 84.7.

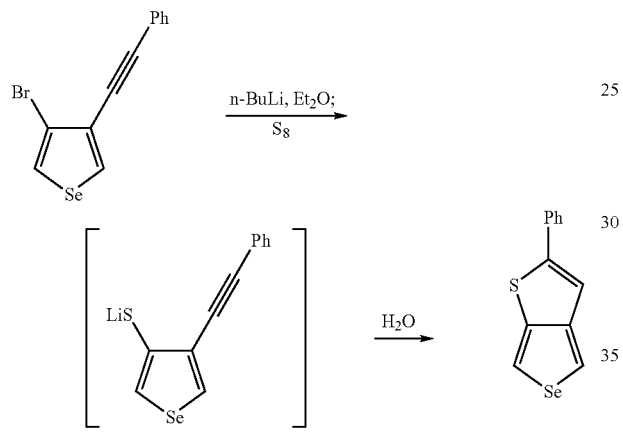

A solution of 3-bromo-4-phenylethynyl-selenophene (1.65 g, 5.32 mmol) in ether (6.00 mL) under $N_2$ was cooled to −70° C. Maintaining the temperature below −50° C., n-butyl lithium (2.5 M in hexanes, 2.13 mL, 5.32 mmol) was added. The reaction was allowed to warm to −30° C. and then was cooled to −50° C. Sulfur (0.179 g, 5.59 mmol) was added in one portion and stirred at 0° C. for 2 h. The solvent was evaporated and a solution of KOH (0.373 g, 6.65 mmol) in methanol (6 mL) was added and heated to reflux for 19 h. Upon cooling to room temperature, the reaction was concentrated, reconstituted in $CH_2Cl_2$ and washed with water. The $CH_2Cl_2$ layer was treated with magnesium sulfate and Darco G60. After filtration and addition of methanol, the $CH_2Cl_2$ was evaporated until the material crystallized out of solution. The crude material was recrystallized from $CH_2Cl_2$/methanol to obtain 2-phenyl-selenolo[3,4-b]thiophene as a light brown solid (0.355 g, 1.35 mmol, 25.4 mol %): 500 MHz $^1$H NMR (DMSO-d$_6$) δ 8.29 (d, J=2.1 Hz, 1H), 8.22 (d, J=1.8 Hz, 1H), 7.68 (d, J=7.3 Hz, 2H), 7.46 (t, J=7.3 Hz, 2H), 7.40-7.37 (m, 2H); 125 MHz $^{13}$C NMR (DMSO-d$_6$) δ 149.8, 148.0, 138.4, 134.3, 129.1, 128.7, 125.5, 120.1, 116.8, 113.7; 95 MHz $^{77}$Se NMR (DMSO-d$_6$) δ 737.2 (t, J {$^{77}$Se-$^1$H}=45.8 Hz); UV-Vis λ$_{max}$=308.2 nm (CH$_2$Cl$_2$); IR (ATR) v 3092, 1552, 1484, 1440, 1329, 1224, 1152, 1069, 1027, 924, 903, 819, 752, 735, 685 cm$^{-1}$; MS (+APCI) m/z (M+1)=265.

While the disclosure has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to any particular embodiment disclosed as the best mode contemplated for carrying out this invention, but that the invention will include all embodiments falling within the scope of the appended claims.

The invention claimed is:

1. A heterocyclic monomer compound according to the following formula:

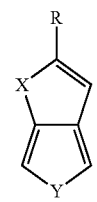

wherein

X is S or Se,

Y is S or Se, wherein one or both of X and Y is Se, and

R is a substituent group selected from the group consisting of hydroxyl, alkyl arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, alkyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, and phenyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, in which one or more non-adjacent $CH_2$ groups in alkyl is optionally replaced, independently, with —O—, —S—, —NH—, —NR'—, —SiR'R"—, —CO—, —COO—, —OCO—, —OCO—O—, —S—CO—, —CO—S—, —CH═CH— or —C:C— in such a manner that O and/or S atoms are not linked directly to one another, each of R' and R", independently, being H, aryl, or alkyl with 1 to 12 C-atoms.

2. The compound of claim 1, wherein R is selected from the group consisting of alkylaryl, arylalkyl, aryl, heteroaryl, $C_1$ to $C_{12}$ primary, secondary or tertiary alkyl groups optionally mono- or polysubstituted by F, Cl, Br, I or CN, phenyl cyclohexyl, naphthalenyl, hydroxyl, alkyl ether, perfluoroaryl, carboxylic acid, sulfonic acid, esters of sulfonic acid, $SF_5$, and F.

3. The compound of claim 1, wherein R is selected from the group consisting of $C_1$ to $C_{12}$ primary, secondary or tertiary alkyl groups and perfluoroalkyl groups.

4. The compound of claim 1, wherein X is Se.

5. The compound of claim 4, wherein Y is Se.

6. The compound of claim 5, wherein R is $C_1$ to $C_{20}$ primary, secondary or tertiary alkyl groups optionally substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties; or phenyl optionally substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties.

7. The compound of claim 6, wherein R is $C_1$ to $C_{12}$ primary, secondary or tertiary alkyl groups optionally substituted with F, Cl, Br, I, or CN.

8. The compound of claim 7, wherein the compound is 2-hexyl- selenolo [3,4-b]selenophene.

9. The compound of claim 6, wherein R is phenyl optionally substituted with F, Cl, Br, I, or CN.

10. The compound of claim 9, wherein the compound is 2-phenyl-selenolo [3,4-b]selenophene.

11. The compound of claim 4, wherein Y is S.

12. The compound of claim 11, wherein R is $C_1$ to $C_{20}$ primary, secondary or tertiary alkyl groups optionally substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties; or phenyl optionally substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties.

13. The compound of claim 12, wherein R is $C_1$ to $C_{12}$ primary, secondary or tertiary alkyl groups optionally substituted with F, Cl, Br, I, or CN.

14. The compound of claim 13, wherein the compound is 2-hexyl-selenolo [2,3-c]thiophene.

15. The compound of claim 12, wherein R is phenyl optionally substituted with F, Cl, Br, I, or CN.

16. The compound of claim 15, wherein the compound is 2-phenyl-selenolo [2,3-c]thiophene.

17. The compound of claim 1, wherein X is S and Y is Se.

18. The compound of claim 17, wherein R is $C_1$ to $C_{20}$ primary, secondary or tertiary alkyl groups optionally substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties; or phenyl optionally substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties.

19. The compound of claim 18, wherein R is $C_1$ to $C_{12}$ primary, secondary or tertiary alkyl groups optionally substituted with F, Cl, Br, I, or CN.

20. The compound of claim 19, wherein the compound is 2-hexyl-selenolo [3,4-b]thiophene.

21. The compound of claim 18, wherein R is phenyl optionally substituted with F, Cl, Br, I, or CN.

22. The compound of claim 21, wherein the compound is 2-phenyl-selenolo [3,4-b]thiophene.

* * * * *

UNITED STATES PATENT AND TRADEMARK OFFICE
CERTIFICATE OF CORRECTION

PATENT NO. : 7,982,055 B2
APPLICATION NO. : 11/777362
DATED : July 19, 2011
INVENTOR(S) : Steffen Zahn, Carrie A. Costello and Mark McLaws It is certified that error appears in the above-identified patent and that said Letters Patent is hereby corrected as shown below:

Title Page Col. 1, Line 2 (Other Publications)
Delete "tetrahydron," and insert -- Tetrahedron, -- therefor.

Title Page Col. 1, Line 4 (Other Publications)
Delete "Thieono" and insert -- Thieno -- therefor.

Title Page Col. 2, Line 1 (Other Publications)
Delete "Thiopene" and insert -- Thiophene -- therefor.

Title Page Col. 2, Line 12 (Other Publications)
Delete "Chemcial" and insert -- Chemical -- therefor.

Title Page Col. 2, Line 19 (Other Publications)
Delete "Dialkynylaromateic" and insert -- Dialkynylaromatic -- therefor.

Title Page Col 2, Line 31 (Other Publications)
Delete "Thiophenese" and insert -- Thiophenes -- therefor.

Title Page Col. 2, Line 34 (Other Publications)
Delete "Selenophtene" and insert -- Selenophene -- therefor.

Col. 26, Line 28
In Claim 1, delete "alkyl" and insert -- alkyl, -- therefor.

Col. 26, Line 29
In Claim 1, delete "perfluororaryl," and insert -- perfluoroaryl, -- therefor.

Col. 26, Line 55
In Claim 2, delete "phenyl" and insert -- phenyl, -- therefor.

Signed and Sealed this
Fourth Day of October, 2011

David J. Kappos
*Director of the United States Patent and Trademark Office*

Page 1 of 1